United States Patent

Dahmen et al.

[11] Patent Number: 5,968,873
[45] Date of Patent: Oct. 19, 1999

[54] SELECTIVE HERBICIDES BASED ON 4-AMINO-5-(1-METHYL-ETHYL)-2-(1,1-DIMETHYLETHYLAMINOCARBONYL)-2,4-DIHYDRO-3H-1,2,4-TRIAZOL-3-ONE

[75] Inventors: Peter Dahmen, Neuss, Germany; Wolfgang Thielert, Bury St. Edmunds, United Kingdom; Klaus-Helmut Müller, Düsseldorf; Hans-Jochem Riebel, Wuppertal, both of Germany

[73] Assignee: Bayer Aktiengesellschaft, Leverkusen, Germany

[21] Appl. No.: 08/917,026

[22] Filed: Aug. 22, 1997

[30] Foreign Application Priority Data

Aug. 30, 1996 [DE] Germany .......................... 196 35 060

[51] Int. Cl.$^6$ .................................................. A01N 43/653
[52] U.S. Cl. ......................... 504/128; 504/129; 504/130; 504/132; 504/134; 504/136; 504/137; 504/139

[58] Field of Search ..................................... 504/139, 128, 504/129, 130, 132, 134, 136, 137

[56] References Cited

U.S. PATENT DOCUMENTS 5,194,085  3/1993  Lindig et al. ............................ 504/273
5,631,210  5/1997  Tseng ...................................... 504/282

*Primary Examiner*—S. Mark Clardy
*Attorney, Agent, or Firm*—Sprung Kramer Schaefer & Briscoe

[57] ABSTRACT

The invention relates to novel herbicidal synergistic active compound combinations comprising, on the one hand, 4-amino-5-(1-methyl-ethyl)-2-(1,1-dimethyl-ethylaminocarbonyl)-2,4-dihydro-3H-1,2,4-triazol-3-one and, on the other hand, known herbicidally active compounds, which can be used particularly successfully for selectively controlling weeds in a variety of crops, in particular in maize and wheat cultures.

16 Claims, No Drawings

SELECTIVE HERBICIDES BASED ON 4-AMINO-5-(1-METHYL-ETHYL)-2-(1,1-DIMETHYLETHYLAMINOCARBONYL)-2,4-DIHYDRO-3H-1,2,4-TRIAZOL-3-ONE

The invention relates to novel herbicidal synergistic active compound combinations comprising, on the one hand, a known carbamoyltriazolinone and, on the other hand, known herbicidally active compounds, which can be used particularly successfully for selectively controlling weeds in a variety of crops.

Carbamoyltriazolinones, which are herbicides with a broad spectrum of action, are the subject of a series of patent applications (cf. EP-294 666, EP-370 293, EP-391 187, EP-398 096, EP-399 294, EP-415 196, EP-477 646). However, the known carbamoyltriazolinones have a number of gaps in their action.

Surprisingly, it has now been found that 4-amino-5-(1-methyl-ethyl)-2-(1,1-dimethyl-ethylaminocarbonyl)-2,4-dihydro-3H-1,2,4-triazol-3-one when used together with known herbicidally active compounds from various substance classes has pronounced synergistic effects with regard to the activity against weeds and can be used particularly advantageously in combination with other herbicides as broad-spectrum combination preparation for the selective control of weeds in crops, such as, for example, in maize and wheat cultures.

The invention accordingly provides selective herbicidal compositions, characterized by an effective content of a combination of active compounds comprising 4-amino-5-(1-methyl-ethyl)-2-( 1,1-dimethyl-ethylaminocarbonyl)-2,4-dihydro-3H-1,2,4-triazol-3-one (active compound) (A)) of the formula

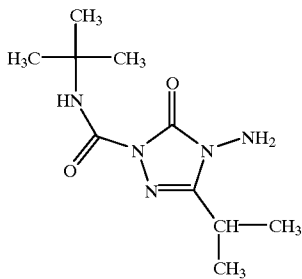

and one or more compounds from a group of herbicides comprising the active compounds listed below:

2-chloro-N-(ethoxymethyl)-N-(2-ethyl-6-methyl-phenyl)-acetamide (acetochlor), 2-chloro-6-nitro-3-phenoxy-benzenamine (aclonifen), 2-chloro-N-(methoxymethyl)-N-(2-diethyl-phenyl)-acetamide (alachlor), N-(4,6-dimethoxy-pyrimidin-2-yl)-N'-(N-methyl-N-methylsulphonyl-sulphamoyl)-urea (amidosulfuron), 6-chloro-4-ethylamino-2-isopropylamino-1,3,5-triazine (atrazine), ethyl N-benzoyl-N-(3,4-dichloro-phenyl)-DL-alaninate (benzoylprop-ethyl), 3-i-propyl-1H-2,1,3-benzothiadiazin-4(3H)-one 2,2-dioxide (bentazone), methyl 5-(2,4-dichloro-phenoxy)-2-nitro-benzoate (bifenox), 2-bromo-3,3-dimethyl-N-(1-methyl-1-phenyl-ethyl)-butanamide (bromobutide), 3,5-dibromo-4-hydroxy-benzaldehyde O-(2,4-dinitro-phenyl)-oxime (bromofenoxim), 3,5-dibromo-4-hydroxy-benzonitrile (bromoxynil), N-(butoxymethyl)-2-chloro-N-(2,6-diethylphenyl)-acetamide (butachlor), S-ethyl bis-(2-methyl-propyl)-thiocarbamate (butylate), 2-(4-chloro-2-fluoro-5-(2-chloro-2-ethoxycarbonyl-ethyl)-phenyl)-4-difluoromethyl-5-methyl-2,4-dihydro-3H-1,2,4-triazol-3-one (carfentrazone-ethyl, F-8426), 2,4-dichloro-1-(3-methoxy-4-nitro-phenoxy)-benzene (chlomethoxyfen), 3-amino-2,5-dichloro-benzoic acid (chloramben), 1,3,5-trichloro-2-(4-nitro-phenoxy)-benzene (chlornitrofen), N-(4-methoxy-6-methyl-1,3,5-triazin-2-yl)-N'-(2-chloro-phenylsulphonyl)-urea (chlorsulfuron-methyl), N'-(3-chloro-4-methylphenyl)-N,N-dimethyl-urea (chlortoluron), N-(4,6-dimethoxy-1,3,5-triazin-2-yl)-N'-(2-(2-methoxy-ethoxy)-phenylsulphonyl)-urea (cinosulfuron), (R)-(2-propinyl)-2-[4-(5-chloro-3-fluoro-pyridin-2-yl-oxy)-phenoxy-propanoate (clodinafop-propargyl), 3,6-dichloro-2-pyridine-2-carboxylic acid (clopyralid), N-(4-6-dimethoxy-pyrimidin-2-yl)-N'-(3-chloro-4-methoxycarbonyl-1-methyl-pyrazol-5-yl-sulphonyl)-urea (clopyrasulfuron-methyl, halosulfuron, NC-319), methyl-3-chloro-2-[(5-ethoxy-7-fluoro[1,2,4]triazolo[1,5-c]pyrimidin-2-yl-sulphonyl)-amino]-benzoate (cloransulam-methyl), 2-chloro-4-ethylamino-6-(1-cyano-1-methyl-ethylamino)-1,3,5-triazine (cyanazine), N-(4,6-dimethoxy-pyrimidin-2-yl)-N'-(2-cyclopropylcarbonyl-phenylsulphonyl)-urea (cyclosulfamuron, AC-322140), 3,6-dichloro-2-methoxy-benzoic acid (dicamba), (R)-2-(2,4-dichloro-phenoxy)-propionic acid (dichlorprop-P), methyl 2-[4-(2,4-dichloro-phenoxy)-phenoxy]-propionate (diclofop-methyl), 1,2-dimethyl-3,5-diphenyl-1H-pyrazolium methyl sulphate (difenzoquat), N-(2,4-difluoro-phenyl)-2-(3-trifluoromethyl-phenoxy)-pyridine-3-carboxamide (diflufenican), 2-chloro-N-(2,4-dimethyl-3-thienyl)-N-(2-methoxy-1-methyl-ethyl)-acetamide (dimethenamide, SAN-582), 2,4-dichloro-phenoxyacetic acid (2,4-D), 2-amino-4-(1-fluoro-1-methyl-ethyl)-6-(1-methyl-2-(3,5-dimethyl-phenoxy)-ethylamino)-1,3,5-triazine (dimexyflam, IDH-1105), 6,7-dihydro-dipyrido-[1,2-a:2',1'-c]pyrazinediium (diquat), S,S'-dimethyl 2-difluoromethyl-4-i-butyl-6-trifluoromethyl-pyridine-3,5-dicarbothioate (dithiopyr), the sodium salt of N-(4,6-dimethoxy-pyrimidin-2-yl)-N'-(3-methoxycarbonyl-6-trifluoromethyl-pyridin-2-yl-sulphonyl)-urea (DPX-KE-459), S-ethyl dipropylthiocarbamate (EPTC), S-(phenylmethyl) N-ethyl-N-(1,2-dimethyl-propyl)-thiocarbamate (esprocarb), ethyl [2-chloro-5-(4-chloro-5-difluoromethoxy-1-methyl-1H-pyrazol-3-yl)-4-fluoro-phenoxy]-acetate (ET-751), (S)-(2-ethoxy-1-methyl-2-oxoethyl) 2-chloro-5-(2-chloro-4-trifluoromethyl-phenoxy)-benzoate (ethoxyfen), N-(4,6-dimethoxy-pyrimidin-2-yl)-N'-(2-ethoxy-phenoxy-sulphonyl)-urea (ethoxysulfuron, HOE-095404), ethyl 2-[4-(6-chloro-benzoxazol-2-yl-oxy)-phenoxy]-propanoate (fenoxaprop-ethyl), isopropyl N-benzoyl-N-(3-chloro-4-fluoro-phenyl)-DL-alaninate (flamprop-isopropyl), isopropylN-benzoyl-N-(3-chloro-4-fluoro-phenyl)-L-alaninate (flamprop-isopropyl-L), methyl N-benzoyl-N-(3-chloro-4-fluoro-phenyl)-DL-alaninate (flamprop-methyl), pentyl [2-chloro-4-fluoro-5-(1,3,4,5,6,7-hexahydro-1,3-dioxo-2H-isoindol-2-yl)-phenoxy]-acetate (flumiclorac-pentyl), ethoxycarbonylmethyl 5-(2-chloro-4-trifluoromethyl-phenoxy)-2-nitro-benzoate (fluoroglycofen-ethyl), 1-(4-chloro-3-(2,2,3,3,3-pentafluoro-propoxymethyl)-phenyl)-5-phenyl-1H-1,2,4-triazole-3-carboxamide (flupoxam), 1-isopropyl-2-chloro-5-(3,6-dihydro-3-methyl-2,6-dioxo-4-trifluoromethyl-1(2H)-pyrimidyl)-benzoate (flupropacil), 9-hydroxy-9H-fluorene-9-carboxylic acid (flurenol), 4-amino-3,5-dichloro-6-fluoro-pyridin-2-yl-oxy)-acetic acid (fluroxypyr), N-(2,6-difluoro-phenyl)-5-methyl-1,2,4-triazolo[1,5-a]-pyrimidine-2-sulphonamide (flumetsulam, DE-498), methyl [(2-chloro-4-fluoro-5-(tetrahydro-3-oxo- 1H,3H-[1,3,4]-thiadiazolo-[3,4-a]-pyridazin-1-ylidene)-amino-phenyl]-thioacetate (fluthiacet-methyl, KIH-9201), 2-amino-4-(hydroxymethylphosphinyl)-butanoic acid (ammonium salt) (glufosinate-(ammonium)), N-phosphonomethyl-glycine (isopropylammonium), (glyphosate, -isopropylammonium), methyl 2-(4,5-dihydro-4-methyl-4-isopropyl-5-oxo-1H-imidazol-2-yl)-4-methyl-benzoate (imazamethabenz-methyl), 2-(4,5-dihydro-4-methyl-4-isopropyl-5-oxo-1H-imidazol-2-yl)-5-methyl-pyridine-3-carboxylic acid (imazamethapyr), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-isopropyl-5-oxo-1H -imidazol-2-yl)-quinoline-3-carboxylic acid (imazaquin), 2-(4,5-dihydro-4-methyl-4-i-propyl-5-oxo-1H-imidazol-2-yl)-5-ethyl-pyridine-3-carboxylic acid (imazethapyr), N-(4,6-dimethoxy-pyrimidin-2-yl)-N'-(2-chloro-imidazo[1,2-a]-pyridin-3-yl-sulphonyl)-urea (imazosulfuron), 4-hydroxy-3, 5-diiodo-benzonitrile (ioxynil), N,N-dimethyl-N'-(4-isopropyl-phenyl)-urea (isoproturon), N-(3-(1-ethyl-1-methyl-propyl)-isoxazol-5-yl)-2,6-dimethoxy-benzamide (isoxaben), (5-cyclopropyl-isoxazol-4-yl)-(2-methylsulphonyl-4-trifluoromethyl-phenyl)-methanone (isoxaflutole, RPA-201772), N'-(3,4-dichloro-phenyl)-N-methoxy-N-methylurea (linuron), (4-chloro-2-methyl-phenoxy)-acetic acid (MCPA), 2-(4-chloro-2-methyl-phenoxy)-propionic acid (mecoprop), 2-chloro-N-(2,6-dimethyl-phenyl)-N-(1H-pyrazol-1-yl-methyl)-acetamide (metazachlor), N'-(4-(3,4-dihydro-2-methoxy-2,4,4-trimethyl-2H -1-benzopyran-7-yl-oxy)-phenyl)-N-methoxy-N-methyl-urea (metobenzuron, UMP-488), N'-(4-bromo-phenyl)-N-methoxy-N-methylurea (metobromuron), 2-chloro-N-(2-ethyl-6-methyl-phenyl)-N(2-methoxy-1-methyl-ethyl)-acetamide (metolachlor), N-(2,6-dichloro-3-methyl-phenyl)-5,7-dimethoxy-1,2,4-triazolo[1,5-a]-pyrimidine-2-sulphonamide (metosulam, DE-511), N'-(3-chloro-4-methoxy-phenyl)-N,N-dimethyl-urea (metoxuron), 4-amino-6-tert-butyl-3-methylthio-1,2,4-triazin-5-(4H)-one (metribuzin), N-(4-methoxy-6-methyl-1, 3,5-triazin-2-yl)-N'-(2-methoxycarbonyl-phenylsulphonyl)-urea (metsulfuron-methyl), 2-(2-naphthyloxy)-N-phenyl-propanamide (naproanilide), N-butyl-N'-(3,4-dichloro-phenyl)-N-methyl-urea (neburon), N-(4,6-dimethoxy-pyrimidin-2-yl)-N'-(3-dimethylcarbamoyl-pyridin-2-yl-sulphonyl)-urea (nicosulfuron), N-(4,6-dimethyl-pyrimidin-2-yl)-N'-(2-oxetan-3-yl-oxycarbonyl-phenylsulphonyl)-urea (oxasulfuron), 1,1'-dimethyl-4,4'-bipyridinium (paraquat), 1-amino-N-(1-ethyl-propyl)-3,4dimethyl-2,6-dinitro-benzene (pendimethalin), N-(4,6-bis-difluoromethoxy-pyrimidin-2-yl)-N'-(2-methoxycarbonyl-phenylsulphonyl)-urea (primisulfuron-methyl), S-phenylmethyl N,N-dipropyl-thiocarbamate (prosulfocarb), N-(4-methoxy-6-methyl-1,3, 5-triazin-2-yl)-N'-(2-(3,3,3-trifluoro-propyl)-phenylsulphonyl)-urea (prosulfuron), 2-chloro-N-(2,6-diethyl-phenyl)-N-(2-propoxy-ethyl)-acetamide (pretilachlor), 2-chloro-N-isopropyl-N-phenyl-acetamide (propachlor), O-(6-chloro-3-phenyl-pyridazin-4-yl) S-octyl thiocarbonate (pyridate), 4-(2,4dichloro-benzoyl)-1,3-dimethyl-5-(4methyl-phenylsulphonyl-oxy)-pyrazole (pyrazolate), 4-(2,4-dichloro-benzoyl-1,3-dimethyl-5-(phenyl-carbonylmethoxy)-pyrazole (pyrazoxyfen), N-(4, 6dimethoxy-pyrimidin-2-yl)-N'-(4-ethoxycarbonyl-1-methyl-pyrazol-5-yl-sulphonyl)-urea (pyrazosulfuron-ethyl), 7-chloro-3-methyl-quinoline-8-carboxylic acid (quinmerac), N-(4,6-dimethoxy-pyrimidin-2-yl)-N'-(3-ethylsulphonyl-pyridin-2-yl-sulphonyl)-urea (rimsulfuron), 6-chloro-2,4-bis-ethylamino-1,3,5-triazine (simazin), 2-(2-chloro-4-methylsulphonyl-benzoyl)-cyclohexane-1,3-dione (sulcotrione), 2-(2,4-dichloro-5-methylsulphonylamino-phenyl)-4-difluoromethyl-5-methyl-2,4-dihydro-3H-1,2,4-triazol-3-one (sulfentrazone, F-6285), N-phosphonomethyl-glycine-trimethylsulphonium (sulfosate), N-(4,6-dimethoxy-pyrimidin-2-yl)-N'-(2-ethylsulphonyl-imidazo [1,2-a]pyridine-3-sulphonamide (sulfosulfuron, MON-37500), 6-chloro-4-ethylamino-2-tert-butylamino-1,3,5-triazine (terbuthylazine), 2-tert-butylamino-4-ethylamino-6-methylthio-1,3,5-triazine (terbutryn), 2-chloro-N-(2,6-dimethyl-phenyl)-N-(3-methoxy-2-thienyl-methyl)-acetamide (thenylchlor), 6-(6,7-dihydro-6,6-dimethyl-3H, 5H-pyrrolo[2,1-c]-1,2,4-thiadiazol-3-ylidenamino)-7-fluoro-4-(2-propinyl)-2H-1,4-benzoxazin-3(4H )-one (thidiazimin), N-(4-methoxy-6-methyl-1,3,5-triazin-2-yl)-N'-(2-methoxycarbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diisopropyl-carbamothioate (triallate), N-(4-methoxy-6-methyl-1,3,5-triazin-2-yl)-N'-[2-(2-chloro-ethoxy)-phenylsulphonyl]-urea (triasulfuron), N-methyl-N-(4-methoxy-6-methyl-1,3, 5triazin-2-yl)-N'-(2-methoxycarbonyl-phenylsulphonyl)-urea (tribenuron-methyl),2-(3,5-dichloro-phenyl)-2-(2,2,2-trichloro-ethyl)-oxirane (tridiphane), 1-amino-2,6-dinitro-N,N-dipropyl-4-trifluoromethyl-benzene (trifluralin) -("active compounds of Group 1").

Of particular interest are herbicidal compositions according to the invention which are characterized by a content of an active compound combination comprising 4-amino-5-(1-methyl-ethyl)-2-(1,1-dimethyl-ethylaminocarbonyl)-2,4-dihydro-3H-1,2,4-triazol-3-one and one to three active compounds of the above-described Group 1 of herbicides.

Of very particular interest are herbicidal compositions according to the invention which are characterized by a content of an active compound combination comprising 4-amino-5-(1-methyl-ethyl)-2-(1,1 -dimethyl-ethylamininocarbonyl)-2,4-dihydro-3H-1,2,4-triazol-3-one and one or two active compounds of the above-described Group 1 of herbicides.

Particular mention as mixing components from the active compounds of Group 1 may be made of:
acetochlor, alachlor, atrazin, bentazon, butylate, clopyralid, cyanazine, 2,4-D, dimethenamide, EPTC, flumetsulam, fluroxypyr, clopyrasulfuron-methyl, imazethapyr, imazaquin, ioxynil, metazachlor, metobenzuron, metolachlor, metribuzin, nicosulfuron, pendimethalin, primisulfuron-methyl, propachlor, prosulfuron, pyridate, rimsulfuron, simazin, sulcotrione, terbuthylazine, thifensulfuron-methyl, trifluralin, metosulam, isoxaflutole, bentazon, bromoxynil, dicamba, 2,4-D, glyphosate (-isopropylammonium), metribuzin, paraquat, diquat, glufosinate(-ammonium), sulfosate.

Surprisingly, it has now been found that the above-defined active compound combinations, in addition to being very well tolerated by crops, have a particularly high herbicidal activity and can be used in a variety of crops, in particular in maize, but additionally also in wheat, barley and rice, for selectively controlling weeds.

Surprisingly, the herbicidal activity of the active compound combinations according to the invention considerably exceeds the total of the activities of the individual active compounds.

This means that there exists not only a complementary action but an unforeseeable synergistic effect. The novel active compound combinations are tolerated well by a large number of crops, and the novel active compound combinations also effectively control weeds which are otherwise difficult to control. The novel active compound combinations are therefore a valuable addition to the selective herbicides.

The active compound combinations according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compound combinations according to the invention is in no way restricted to these genera, but also extends in the same manner to other plants.

At specific concentration ratios, the synergistic effect of the active compound combinations according to the invention is particularly pronounced. However, the ratios by weight of the active compounds in the active compound combinations can be varied within relatively wide ranges. In general, 0.001 to 1000 parts by weight, preferably 0.01 to 100 parts by weight and particularly preferably 0.1 to 10 parts by weight of one or more active compound(s) of Group 1 are used per part by weight of active compound (A).

The active compound combinations can be converted into the customary formulations, such as solutions, emulsions, wettable powders, suspensions, powders, dusts, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:
for example ammonium salts and ground natural minerals, such as kaolins, clays, talc, chalk, quartz, attapulgite, montmorillonite or diatomaceous earth, and ground synthetic minerals, such as finely divided silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives may be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight, preferably between 0.5 and 90%, of each of the two above-defined groups of active compounds (A) and 1.

In general, the active compound combinations according to the invention are applied in the form of ready mixes. However, the active compounds which the active compound combinations comprise can also be formulated individually and mixed upon use, i.e. applied in the form of tank mixes.

The novel active compound combinations can be used as such or in the form of their formulations, and furthermore also as mixtures with other known herbicides, ready mixes or tank mixes again being possible. They may also be mixed with other known active compounds, such as fungicides, insecticides, acaricides, nematicides, bird repellents, growth substances, plant nutrients and agents which improve soil structure. For particular application purposes, in particular when applied post-emergence, it may furthermore be advantageous to incorporate, in the formulations, mineral or vegetable oils which are tolerated by plants (for example the commercial product "Oleo DuPont 11E") or ammonium salts such as, for example, ammonium sulphate or ammonium thiocyanate, as further additives.

The novel active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The active compound combinations according to the invention can be applied before and after the plants have emerged, that is to say pre-emergence and post-emergence. They can also be incorporated into the soil before sowing.

The active compound combinations of active compound A and Group 1 according to the invention can be used (a) in the conventional cultivation of maize ("conventional tillage"), by the pre-emergence method and by the post-emergence method or (b) in the soil-preserving cultivation of maize ("preplant burndown").

Suitable mixing partners for the conventional cultivation of maize are in particular the following known active compounds (the common names or, alternatively, known codes are given in each case):

acetochlor, alachlor, atrazin, bentazon, butylate, clopyralid, cyanazine, 2,4-D, dimethenamide, EPTC, flumetsulam, fluroxypyr, clopyrasulfuron-methyl, imazethapyr, imazaquin, ioxynil, metazachlor, metobenzuron, metolachlor, metribuzin, nicosulfuron, pendimethalin, primisulfuron-methyl, propachlor, prosulfuron, pyridate, rimsulfuron, simazin, sulcotrione, terbuthylazine, thifensulfuron-methyl, trifluralin, metosulam, isoxaflutole.

Suitable mixing partners for the soil-preserving cultivation of maize are in particular the following known active compounds:

bentazon, bromoxynil, dicamba, 2,4-D, glyphosate(-isopropylammonium), metribuzin, paraquat, diquat, glufosinate(-ammonium), sulfosate.

The applications rates of the active compound combinations according to the invention can vary within a certain range; they depend, inter alia, on the weather and on the soil parameters. In general, the application rates are between 10 g and 10 kg per ha, preferably between 50 g and 5 kg per ha, particularly preferably between 100 g and 2 kg per ha.

The good herbicidal activity of the novel active compound combinations can be seen from the examples which follow. While the individual active compounds show weak points regarding the herbicidal activity, the combinations, without exception, display a very good activity against weeds, which exceeds a simple additive effect.

A synergistic effect in herbicides is always present when the herbicidal activity of the active compound combination exceeds the activity of the active compounds when applied individually.

The expected activity for a given combination of two herbicides can be calculated as follows (cf. COLBY, S. R.: "Calculating synergistic and antagonistic responses of herbicide combinations", Weeds 15, pages 20–22, 1967):

If X=% damage caused by herbicide A (active compound of the formula A) at application rate of p kg/ha
and Y=% damage caused by herbicide B (individual active compound of Group 1) at application rate of q kg/ha
and E=the expected damage of herbicides A and B at application rates of p and q kg/ha,
then $E = X + Y - (X*Y/100)$.

If the actual damage exceeds the calculated figure, the activity of the combination is superadditive, i.e. it shows a synergistic effect.

It can be seen from the examples which follow that the observed herbicidal activity of the active compound combinations according to the invention in the weeds exceeds the calculated activity, i.e. that the novel active compound combinations act synergistically.

USE EXAMPLES

Example A

Pr-emergence test/outdoor

Solvent: 5 parts by weight of acetone

Emulsifier: 1 part by weight of alkylaryl polyglycol ether

To produce a suitable preparation of active compound, 1 part by weight of the active compound combination according to the invention is in each case mixed with the stated amount of solvent, the stated amount of emulsifier is added and the concentrate is diluted with water to the desired concentration.

Shortly after the seeds of the test plants have been sown outdoors, the individual plots are watered with the amount of active compound preparation required for wetting the soil surface uniformly. The active compound concentration in the preparation is of no importance, only the application rate of active compounds per unit area being decisive.

After 5 weeks, the degree of damage to the test plants is scored in % damage in comparison with the development of the untreated control. The figures denote:

0%=no action

100%=total destruction.

In this test, for example a combination of active compound (A) and isoxaflutole has a superadditive, i.e. synergistic, activity against a number of weeds.

TABLE A

| | | Pre-emergence test (outdoor) | | | | |
|---|---|---|---|---|---|---|
| Active compound(s) | Application rate (g a.i./ha) | Brachiaria Plantaginea | Cenchrus Echinatus | Bidens Pilosa | Ipomoea Spec. | Raphanus Raphanistrum |
| Active compound (A) 7S WG | 280 | 15 | 40 | 40 | 35 | 55 |
| Isoxaflutole 75 WG | 75 | 65 | 60 | 40 | 45 | 50 |
| Active compound (A) 70 WG + isoxaflutole 75 WG | 280 + 75 | 75 (E = 70.25) | 78 (E = 76) | 92 (E = 64) | 75 (E = 64.25) | 96 (E = 91) |

We claim:

1. Selective herbicidal compositions, comprising an effective amount of a combination of active compounds comprising 4-amino-5-(1-methyl-ethyl)-2-(1,1-dimethyl-ethylaminocarbonyl)-2,4-dihydro-3H-1,2,4-triazol-3-one of the formula (A)

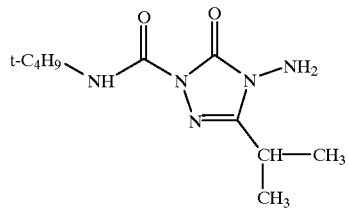

(A)

and one or more compounds from a group of herbicides comprising the active compounds listed below:
2-chloro-N-(ethoxymethyl)-N-(2-ethyl-6-methyl-phenyl)-acetamide (acetochlor), 2-chloro-6-nitro-3-phenoxy-benzenamine (aclonifen), 2-chloro-N-(methoxymethyl)-N-(2-diethyl-phenyl)-acetamide (alachlor), N-(4,6-dimethoxy-pyrimidin-2-yl)-N'-(N-methyl-N-methylsulphonyl-sulphamoyl)-urea (amidosulfuron), 6-chloro-4-ethylamino-2-isopropylamino-1,3,5-triazine (atrazine), ethyl N-benzoyl-N-(3,4-dichloro-phenyl)-DL-alaninate(benzoylprop-ethyl), 3-i-propyl-1H -2,1,3-benzothiadiazin-4(3H )-one 2,2-dioxide (bentazone), methyl 5-(2,4-dichloro-phenoxy)-2-nitro-benzoate (bifenox), 2-bromo-3,3-dimethyl-N-(1-methyl-1-phenyl-ethyl)-butanamide (bromobutide), 3,5-dibromo-4-hydroxy-benzaldehyde O-(2,4-dinitro-phenyl)-oxime (bromofenoxim), 3,5-dibromo-4-hydroxy-benzonitrile (bromoxynil), N-(butoxymethyl)-2-chloro-N-(2,6-diethylphenyl)-acetamide (butachlor), S-ethyl bis-(2-methyl-propyl)-thiocarbamate (butylate), 2-(4-chloro-2-fluoro-5-(2-chloro- 2-ethoxycarbonyl-ethyl)-phenyl)-4-difluoromethyl-5-methyl-2,4-dihydro-3H -1,2,4-triazol-3-one (carfentrazone-ethyl, F -8426), 2,4-dichloro-1-(3-methoxy-4-nitro-phenoxy)-benzene (chlomethoxyfen), 3-amino-2,5-dichloro-benzoic acid (chloramben), 1,3,5-trichloro-2-(4-nitro-phenoxy)-benzene (chlornitrofen), N-(4-methoxy-6-methyl-1,3,5-triazin-2-yl)-N'-(2-chloro-phenylsulphonyl)-urea (chlorsulfuron-methyl), N'-(3-chloro-4-methylphenyl)-N,N-dimethyl-urea (chlortoluron), N-(4,6-dimethoxy-1,3,5-triazin-2-yl)-N'-(2-(2-methoxy-ethoxy)-phenylsulphonyl)-urea (cinosulfuron), (R)-(2-propinyl)-2-[4-(5-chloro-3-fluoro-pyridin-2-yl-oxy)-phenoxy-propanoate (clodinafop-propargyl), 3,6-dichloro-2-pyridine-2-carboxylic acid (clopyralid), N-(4-6-dimethoxy-pyrimidin-2-yl)-N'-(3-chloro-4-methoxycarbonyl-1-methyl-pyrazol-5-yl-sulphonyl)-urea (clopyrasulfuron-methyl, halosulfuron, NC-319), methyl-3-chloro-2-[(5-ethoxy-7-fluoro[1,2,4]triazolo[1,5-c]pyrimidin-2-yl-sulphonyl)-amino]-benzoate (cloransulam-methyl), 2-chloro-4-ethylamino-6-(1-cyano-1-methyl-ethylamino)-1,3,5-triazine (cyanazine), N-(4,6-dimethoxy-pyrimidin-2-yl)-N'-(2-cyclopropylcarbonyl-phenylsulphonyl)-urea (cyclosulfamuron, AC-322140), 3,6-dichloro-2-methoxy-benzoic acid (dicamba), (R)-2-(2,4-dichloro-phenoxy)-propionic acid (dichlorprop-P), methyl 2-[4-(2,4-dichloro-phenoxy)-phenoxy]-propionate (diclofop-methyl), 1,2-dimethyl-3,5-diphenyl-1H-pyrazolium methyl sulphate (difenzoquat), N-(2,4-difluoro-phenyl)-2-(3-trifluoromethyl-phenoxy)-pyridine-3-carboxamide (diflufenican), 2-chloro-N-(2,4-dimethyl-3-thienyl)-N-(2-methoxy-1-methyl-ethyl)-acetamide (dimethenamid, SAN-582), 2,4-dichloro-phenoxyacetic acid (2,4-D), 2-amino-4-(1-fluoro-1-methyl-ethyl)-6-(1-methyl-2-(3,5-dimethyl-phenoxy)-ethylamino)-1,3,5-triazine (dimexyflam, IDH-1105), 6,7-dihydro-dipyrido-[1,2-a:2',1'-c]pyrazinediium (diquat), S,S'-dimethyl 2-difluoromethyl-4-i-butyl-6-trifluoromethyl-pyridine-3,5-dicarbothioate (dithiopyr), the sodium salt of N-(4,6-dimethoxy-pyrimidin-2-yl)-N'-(3-methoxycarbonyl-6-trifluoromethyl-pyridin-2-yl-sulphonyl)-urea (DPX-KE-459), S-ethyl dipropylthiocarbamate (EPTC), S-(phenylmethyl) N-ethyl-N-(1,2-dimethyl-propyl)-thiocarbamate (esprocarb), ethyl [2-chloro-5-(4-chloro-5-difluoromethoxy-1-methyl-1H-pyrazol-3-yl)-4-fluoro-phenoxy]-acetate (ET-751), (S)-(2-ethoxy-1-methyl-2-oxoethyl) 2-chloro-5-(2-chloro-4-trifluoromethyl-phenoxy)-benzoate (ethoxyfen), N-(4,6-dimethoxy-pyrimidin-2-yl)-N'-(2-ethoxy-phenoxy-sulphonyl)-urea (ethoxysulfuron, HOE-095404), ethyl 2-[4-(6-chloro-benzoxazol-2-yl-oxy)-phenoxy]-propanoate (fenoxaprop-ethyl), isopropyl N-benzoyl-N-(3-chloro-4-fluoro-phenyl)-DL-alaninate (flamprop-isopropyl), isopropyl N-benzoyl-N-(3-chloro-4-fluoro-phenyl)-L-alaninate (flamprop-isopropyl-L), methyl N-benzoyl-N-(3-chloro-4-fluoro-phenyl)-DL-alaninate (flamprop-methyl), pentyl [2-chloro-4-fluoro-5-(1,3,4,5,6,7-hexahydro-1,3-dioxo-2H-isoindol-2-yl)-phenoxy]-acetate (flumiclorac-pentyl), ethoxycarbonylmethyl 5-(2-chloro-4-trifluoromethyl-phenoxy)-2-nitro-benzoate (fluoroglycofen-ethyl), 1-(4-chloro-3-(2,2,3,3,3-pentafluoro-propoxymethyl)-phenyl)-5-phenyl-1H-1,2,4-triazole-3-carboxamide (flupoxam), 1-isopropyl-2-chloro-5-(3,6-dihydro-3-methyl-2,6-dioxo-4-trifluoromethyl-1(2H)-pyrimidyl)-benzoate (flupropacil), 9-hydroxy-9H-fluorene-9-carboxylic acid (flurenol), 4-amino-3,5-dichloro-6-fluoro-pyridin-2-yl-oxy)-acetic acid (fluroxypyr), N-(2,6-difluoro-phenyl)-5-methyl-1,2,4-triazolo[1,5-a]-pyrimidine-2-sulphonamide (flumetsulam, DE-498), methyl [(2-chloro-4-fluoro-5-(tetrahydro-3-oxo-1H,3H-[1,3,4]-thiadiazolo-[3,4-a]-pyridazin-1-ylidene)-amino-phenyl]-thioacetate (fluthiacet-methyl, KIH-9201), 2-amino-4-(hydroxymethylphosphinyl)-butanoic acid (ammonium salt) (glufosinate-(ammonium)), N-phosphonomethyl-glycine (isopropylammonium), (glyphosate, -isopropylammonium), methyl 2-(4,5-dihydro-4-methyl-4-isopropyl-5-oxo-1H-imidazol-2-yl)-4-methyl-benzoate (imazamethabenz-methyl), 2-(4,5-dihydro-4-methyl-4-isopropyl-5-oxo-1H-imidazol-2-yl)-5-methyl-pyridine-3-carboxylic acid (imazamethapyr), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-isopropyl-5-oxo-1H-imidazol-2-yl)-quinoline-3-carboxylic acid (imazaquin), 2-(4,5-dihydro-4-methyl-4-i-propyl-5-oxo-1H-imidazol-2-yl)-5-ethyl-pyridine-3-carboxylic acid (imazethapyr), N-(4,6-dimethoxy-pyrimidin-2-yl)-N'-(2-chloro-imidazo[1,2-a]-pyridin-3-yl-sulphonyl)-urea (imazosulfuron), 4-hydroxy-3,5-diiodo-benzonitrile (ioxynil), N,N-dimethyl-N'-(4-isopropyl-phenyl)-urea (isoproturon), N-(3-(1-ethyl-1-methyl-propyl)-isoxazol-5-yl)-2,6-dimethoxy-benzamide (isoxaben), (5-cyclopropyl-isoxazol-4-yl)-(2-methylsulphonyl-4-trifluoromethyl-phenyl)-methanone (isoxaflutole, RPA-201772), N'-(3,4-dichloro-phenyl)-N-methoxy-N-methylurea (linuron), (4-chloro-2-methyl-phenoxy)-acetic acid (MCPA), 2-(4-chloro-2-methyl-phenoxy)-propionic acid (mecoprop), 2-chloro-N-(2,6-dimethyl-phenyl)-N-(1H-pyrazol-1-yl-methyl)-acetamide (metazachlor), N'-(4-(3,4-dihydro-2-methoxy-2,4,4-trimethyl-2H-1-benzopyran-7-yl-oxy)-phenyl)-N-methoxy-N-methyl-urea (metobenzuron, UMP-488), N'-(4-bromo-phenyl)-N-methoxy-N-methylurea (metobromuron), 2-chloro-N-(2-ethyl-6- methyl-phenyl)-N-(2-methoxy-1-methyl-ethyl)-acetamide (metolachlor), N-(2,6-dichloro-3-methyl-phenyl)-5,7-dimethoxy-1,2,4-triazolo[1,5-a]-pyrimidine-2-sulphonamide(metosulam, DE-511), N'-(3-chloro-4-methoxy-phenyl)-N,N-dimethyl-urea (metoxuron), 4-amino-6-tert-butyl-3-methylthio-1,2,4-triazin-5-(4H)-one (metribuzin), N-(4-methoxy-6-methyl-1,3,5-triazin-2-yl)-N'-(2-methoxycarbonyl-phenylsulphonyl)-urea (metsulfuron-methyl), 2-(2-naphthyloxy)-N-phenyl-propanamide (naproanilide), N-butyl-N'-(3,4-dichloro-phenyl)-N-methyl-urea(neburon),N-(4,6-dimethoxy-pyrimidin-2-yl)-N'-(3-dimethylcarbamoyl-pyridin-2-yl-sulphonyl)-urea (nicosulfuron), N-(4,6-dimethyl-pyrimidin-2-yl)-N'-(2-oxetan-3-yl-oxycarbonyl-phenylsulphonyl)-urea (oxasulfuron), 1,1'-dimethyl-4,4'-bipyridinium (paraquat), 1-amino-N-(1-ethyl-propyl)-3,4-dimethyl- 2,6-dinitro-benzene (pendimethalin), N-(4,6-bis-difluoromethoxy-pyrimidin-2-yl)-N'-(2-methoxycarbonyl-phenylsulphonyl)-urea (primisulfuron-methyl), S-phenylmethyl N,N-dipropyl-thiocarbamate (prosulfocarb), N-(4-methoxy-6-methyl-1,3,5-triazin-2-yl)-N'-(2-(3,3,3-trifluoro-propyl)-phenylsulphonyl)-urea (prosulfuron), 2-chloro-N-(2,6-diethyl-phenyl)-N-(2-propoxy-ethyl)-acetamide (pretilachlor), 2-chloro-N-isopropyl-N-phenyl-acetamide (propachlor), O-(6-chloro-3-phenyl-pyridazin-4-yl) S-octyl thiocarbonate (pyridate), 4-(2,4-dichloro-benzoyl)-1,3-dimethyl-5-(4-methyl-phenylsulphonyl-oxy)-pyrazole (pyrazolate), 4-(2,4-dichloro-benzoyl-1,3-dimethyl-5-(phenyl-carbonylmethoxy)-pyrazole (pyrazoxyfen), N-(4,6-dimethoxy-pyrimidin-2-yl)-N'-(4-ethoxycarbonyl-1-methyl-pyrazol-5-yl-sulphonyl)-urea (pyrazosulfuron-ethyl), 7-chloro-3-methyl-quinoline-8-carboxylic acid (quinmerac), N-(4,6-dimethoxy-pyrimidin-2-yl)-N'-(3-ethylsulphonyl-pyridin-2-yl-sulphonyl)-urea (rimsulfuron), 6-chloro-2,4-bis-ethylamino-1,3,5-triazine (simazin), 2-(2-chloro-4-methylsulphonyl-benzoyl)-cyclohexane-1,3-dione (sulcotrione), 2-(2,4-dichloro-5-methylsulphonylamino-phenyl)-4-difluoromethyl-5-methyl-2,4-dihydro-3H-1,2,4-triazol-3-one (sulfentrazone, F -6285), N-phosphonomethyl-glycine-trimethylsulphonium (sulfosate), N-(4,6-dimethoxy-pyrimidin-2-yl)-N'-(2-ethylsulphonyl-imidazo[1,2-a]pyridine-3-sulphonamide (sulfosulfuron, MON-37500), 6-chloro-4-ethylamino-2-tert-butylamino-1,3,5-triazine (terbuthylazine), 2-tert-butylamino-4-ethylamino-6-methylthio-1,3,5-triazine (terbutryn), 2-chloro-N-(2,6-dimethyl-phenyl)-N-(3-methoxy-2-thienyl-methyl)-acetamide (thenylchlor), 6-(6,7-dihydro-6,6-dimethyl-3H,5H-pyrrolo[2,1-c]-1,2,4-thiadiazol-3-ylidenamino)-7-fluoro-4-(2-propinyl)-2H-1,4-benzoxazin-3(4H)-one (thidiazimin), N-(4-methoxy-6-methyl-1,3,5-triazin-2-yl)-N'-(2-methoxycarbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diisopropylcarbamothioate (triallate), N-(4-methoxy-6-methyl-1,3,5-triazin-2-yl)-N'-[2-(2-chloro-ethoxy)-phenylsulphonyl]-urea (triasulfuron), N-methyl-N-(4-methoxy-6-methyl-1,3,5-triazin-2-yl)-N'-(2-methoxycarbonyl-phenylsulphonyl)-urea (tribenuron-methyl), 2-(3,5-dichloro-phenyl)-2-(2,2,2-trichloro-ethyl)-oxirane (tridiphane), 1-amino-2,6-dinitro-N,N-dipropyl-4-trifluoromethyl-benzene (trifluralin) -("active compounds of Group 1").

2. Selective herbicidal compositions according to claim 1, wherein 0.001 to 1000 parts by weight of one or more active compounds of Group 1 are used per part by weight of the active compound (A).

3. Selective herbicidal compositions according to claim 1, wherein the mixing partners of Group 1 are at least one of acetochlor, dimethenamide, 2,4-D, flumetsulam, metosulam, metolachlor, and isoxaflutole.

4. A selective herbicide comprising an herbicidally effective amount of an active compound combination according to claim 1 and a diluent for controlling undesirable plants.

5. A selective herbicide comprising an herbicidally effective amount of an active compound combination according to claim 1 mixed with extenders and/or surface-active substances for controlling undesirable plants.

6. A selective herbicide for use in maize, wheat, barley and rice comprising an herbicidally effective amount of an active compound combination according to claim 1 and a diluent for controlling undesirable plants.

7. Selective herbicidal compositions according to claim 6, wherein the mixing partners of Group 1 used in conventional maize cultivation are acetochlor, alachlor, atrazin, bentazon, butylate, clopyralid, cyanazine, 2,4-D, dimethenamide, EPTC, flumetsulam, fluroxypyr, clopyrasulfuron-methyl, imazethapyr, imazaquin, ioxynil, metazachlor, metobenzuron, metolachlor, metribuzin, nicosulfuron, pendimethalin, primisulfuron-methyl, propachlor, prosulfuron, pyridate, rimsulfuron, simazin, sulcotrione, terbuthylazine, thifensulfuron-methyl, trifluralin, metosulam, isoxaflutole.

8. Selective herbicidal compositions according to claim 6, wherein the mixing partners of Group 1 used in soil-preserving maize cultivation are bentazon, bromoxynil, dicamba, 2,4-D, glyphosate(-isopropylammonium), metribuzin, paraquat, diquat, glufosinate(-ammonium) sulfoxate, sulfosate.

9. A selective herbicide for conventional maize cultivation or in soil-preserving maize cultivation comprising an herbicidally effective amount of an active compound combination according to claim 1 and a diluent for controlling undesirable plants.

10. Selective herbicidal compositions comprising an effective amount of an active compound combination comprising 4-amino-5-(1-methyl-ethyl)-2-(1,1-dimethyl-ethylaminocarbonyl)-2,4-dihydro-3H-1,2,4-triazol-3-one of the formula A

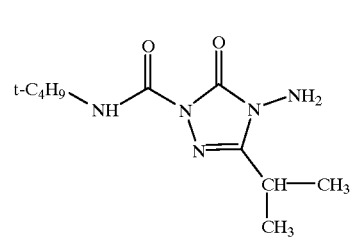

(A)

and isoxaflutole.

11. A selective herbicide comprising an herbicidally effective amount of an active compound combination according to claim 10 and a diluent for controlling undesirable plants.

12. Selective herbicidal compositions according to claim 10, wherein 0.001 to 1000 parts by weight of isoxaflutole are used per part by weight of the active compound (A).

13. Method for controlling undesirable plants comprising applying an herbicidally effective amount of an active compound combination according to claim 1 to the undesirable plants or their habitat or to an area from which one desires to exclude such plants.

14. Method for controlling undesirable plants in maize, wheat, barley and rice comprising applying an herbicidally effective amount of an active compound combination according to claim 1 to the undesirable plants or their habitat or to an area from which one desires to exclude such plants, such habitat or area being in maize, wheat, barley and rice.

15. Method for controlling undesirable plants in conventional maize cultivation or in soil-preserving maize cultivation comprising applying an herbicidally effective amount of an active compound combination according to claim 1 to the undesirable plants or their habitat or to an area from which one desires to exclude such plants, such habitat or area being in conventional maize cultivation or in soil-preserving maize cultivation.

16. Method for controlling undesirable plants comprising applying an herbicidally effective amount of an active compound combination according to claim 10 to the undesirable plants or their habitat or to an area from which one desires to exclude such plants.

* * * * *